United States Patent [19]

Preziuso et al.

[11] 4,251,259
[45] Feb. 17, 1981

[54] SYNERGISTIC COMPOSITIONS OF FUSICOCCYN AND HERBICIDES

[75] Inventors: Ciro Preziuso, Milan; Marco Radice, Corsico; Giorgio Siddi, S. Donato Milanese; Ernesto Signorini, Malnate, all of Italy

[73] Assignee: Montedison S.p.A., Milan, Italy

[21] Appl. No.: 958,616

[22] Filed: Nov. 8, 1978

[30] Foreign Application Priority Data

Nov. 10, 1977 [IT] Italy ................. 29530 A/77

[51] Int. Cl.$^3$ ........................................... A01N 43/16
[52] U.S. Cl. ........................................... 71/88; 71/93; 71/94; 71/111; 71/117; 71/120
[58] Field of Search ........................................ 71/94, 88

[56] References Cited

U.S. PATENT DOCUMENTS 4,104,052  8/1978  Szrrybalo ................. 71/88

OTHER PUBLICATIONS

Turner et al., Nature, vol. 223, pp. 1070–1071.
Caldogno et al., Giornale Botanico Italiano, vol. 103, pp. 629–630.
Lado et al., Informatore Botanico Italiano, vol. 4, p. 78.
Chain et al., Chem. Abst., vol. 78, 53478d.

Primary Examiner—Catherine L. Mills

[57] ABSTRACT

The effectiveness of herbicides in general is enhanced, or boosted, by using them in combination with the glucoside, fusicoccyn.

8 Claims, No Drawings

SYNERGISTIC COMPOSITIONS OF FUSICOCCYN AND HERBICIDES

THE PRIOR ART

The glucoside, fusicoccyn, is known, having been isolated and identified by A. Ballio et al from culture filtrates of *Fusicoccum Amygdali Del*, a fungus responsible for cancer in almond and peach trees, (see, for instance, Experientia 24, pp. 631-635).

The phytotoxic action of fusicoccyn on certain fungi is also known, for example its phytotoxic action on *Prunus Amygdali* (see A. Graniti, Phytopatologia Mediterranea, 1, pp. 182-185) as well as on other pruni (see V. Piglionica, ibid, pp. 96-100); on the opening of foliar stomata (see N. C. Turner and A. Graniti, Nature, 223, pp. 1070-1071); and on cellular elongation (see F. Ras i Caldogno et al, Giornale Botanico Italiano, 103, pp. 629-630; and Lado et al Informatore Botanico Italiano 4, p. 78).

However, the extensive literature referring to fusicoccyn, with which we are familiar, does not suggest any practical, commercial application of it.

THE PRESENT INVENTION

One object of this invention is to provide herbicidal compositions the essential constitutents of which are herbicides and fusicoccyn.

Another object is to provide a method for enhancing, or boosting, the effectiveness of herbicides by using them in combination with fusicoccyn.

These and other objects are achieved by the present invention based on our finding of synergism between fusicoccyn and herbicides in general.

Thus, we have found that by applying herbicides in combination with fusicoccyn in quantities of at least 0.02 kg/ha of the surface treated, the activity of the herbicides is boosted to a surprising extent, independently of the nature of the herbicide or how it acts, and without influence on the selectivity of the herbicides with regard to useful plants to which they are normally applied.

The herbicides and fusicoccyn can be applied to the plants to be protected either separately or in admixture. The composition applied to the plants, whether the herbicide and fusicoccyn are applied separately or in admixture, can be in the form of powders, solutions or suspensions which may contain various adjuvants such as surfactants, inert carriers, etc. The amount of fusicoccyn used in conjunction with the herbicides to result in the enhanced effectiveness of the herbicides varies widely, starting with a lower limit of 0.02 kg/ha of the treated plant surface. In a preferred embodiment, the amount of fusicoccyn used is from 0.1% by weight to double the weight of the herbicide or mixture of herbicides.

As shown in the Tables infra, the enhancing or boosting effect of the fusicoccyn is realized both in greenhouses and in the field.

Although the specific examples given herein—which are provided to illustrate the invention in more detail and are not intended to be limiting—show the effectiveness of fusicoccyn in enhancing the effectiveness of herbicides which are, respectively, carbamates, quaternary derivatives of diprydilium, phenoxy derivatives, triazines and ureic herbicide derivatives, the enhancing effect of fusicoccyn is general for all post-emergence herbicides, as also appears from the constancy of the results obtained with variously classified herbicides which differ completely from each other in regard to the mechanisms by which they act.

EXAMPLE 1

BOOSTING THE ACTIVITY OF HERBICIDES BY MEANS OF FUSICOCCYN IN THE LABORATORY

Pots of 10 cm diameter and 10 cm high were filled with sandy soil and in each of them was then sown one of the following infestants: *ECHINOCHLOA CRUS-GALLI*, IPOMOEA Spp, *STELLARIA MEDIA, GALIUM APARINE, VIGNA SINENSIS,* SORGHUM Spp, *ALISMA PLANTAGO*.

All the pots were kept in conditioned rooms under the following conditions: temperatures comprised between 15° and 24° C., relative humidity 70%, photoperiod 12 hours, light intensity corresponding to 2500 lux. Every two days, the pots were uniformly watered so as to ensure a degree of humidity sufficient for good development of the plants.

After 15 days from the sowing, all the small plants, 10-15 cm high, were sprinkled with fusicoccyn in the form of a hydroacetonic dispersion with the herbicide products under examination in the form of an aqueous dispersion, or with a mixture of fusicoccyn with each herbicide obtained by pouring the fusicoccyn hydroacetonic dispersion into the aqueous dispersion of the herbicide. The amount of sprinkled liquid was equal to 2000 lt/ha.

After the treatment, the plants were maintained under observation in the same conditioned rooms. Several hours after the treatment, evaluations were made according to a scale of values from 0 to 9, where 0=no activity at all, 9—total activity. (See Tables Nos. I to V inclusive).

TABLE I

| | | | \multicolumn{12}{c}{BOOSTING OF HERBICIDE ACTIVITY IN THE LABORATORY} |
|---|---|---|---|---|---|---|---|---|---|---|---|---|---|
| | | | \multicolumn{12}{c}{TIME LAPSED BETWEEN TREATMENT AND DETERMINATION OF RESULTS} |
| | DOSE | | 2 Hours | | | | 5 Hours | | | | 20 Hours | | | |
| PRODUCT | ppm | a.p.kg/ha | Echin-ochloa | Ipo-moea | Stel-laria | Ga-lium | Echin-ochloa | Ipo-moea | Stel-laria | Ga-lium | Echin-ochloa | Ipo-moea | Stel-laria | Ga-lium |
| FUSICOCCYN | 50 | 0.1 | 0 | 1 | 1 | 1 | 0 | 1 | 1 | 1 | 1 | 4 | 1 | 3 |
| PARAQUAT | 50 | 0.1 | 0 | 0 | 2 | 0 | 0 | 0 | 3 | 0 | 1 | 1 | 4 | 1 |
| MIXTURE OF PARAQUAT AND FUSICOCCYN | 50 + 50 | 0.1 + 0.1 | 4 | 4 | 5 | 3 | 4 | 5 | 7 | 4 | 5 | 6 | 8 | 6 |

| | TIME LAPSED BETWEEN TREATMENT AND DETERMINATION OF RESULTS | |
|---|---|---|
| | 120 Hrs.(5 days) | 480 Hrs.(20 d.) |

TABLE I-continued

| | | | Echin- | Ipo- | Stel- | Ga- | Echin- | Ipo- | Stel- | Ga- |
|---|---|---|---|---|---|---|---|---|---|---|
| PRODUCT | DOSE ppm | a.p.kg/ha | ochloa | moea | laria | lium | ochloa | moea | laria | lium |
| FUSICOCCYN | 50 | 0.1 | 1 | 5 | 2 | 3 | 1 | 5 | 2 | 3 |
| PARAQUAT | 50 | 0.1 | 1 | 1 | 6 | 1 | 2 | 1 | 7 | 6 |
| MIXTURE OF PARAQUAT AND FUSICOCCYN | 50 + 50 | 0.1 + 0.1 | 5 | 6 | 8 | 6 | 5 | 6 | 8 | 6 | a.p. = active principle
Paraquat = 1,1'dimethyl-4,4'-dipyridilium chloride

TABLE II

BOOSTING OF HERBICIDE ACTIVITY IN THE LABORATORY

TIME LABSED BETWEEN TREATMENT AND DETERMINATION OF RES.

| | DOSE | | 120 Hours (5 days) | | | | | 168 Hours (7 days) | | | | | 480 Hours (20 days) | | | | |
|---|---|---|---|---|---|---|---|---|---|---|---|---|---|---|---|---|---|
| PRODUCT | ppm | a.p. kg/ha | Echin-ochloa | Stel-laria | Ga-lium | A-lisma | Sor-ghum | Echin-ochloa | Stel-laria | Ga-lium | A-lisma | Sor-ghum | Echin-ochloa | Stel-laria | Ga-lium | A-lisma | Sor-ghum |
| FUSICOCCYN | 50 | 0.1 | 1 | 2 | 1 | 0 | 1 | 1 | 2 | 2 | 1 | 1 | 1 | 2 | 2 | 1 | 1 |
| 2,4 D | 125 | 0.25 | 0 | 2 | 0 | 1 | 0 | 1 | 2 | 0 | 3 | 1 | 1 | 2 | 0 | 3 | 1 |
| MIXTURE OF 2,4 D AND FUSICOCCYN | 125 + 50 | 0.25 + 0.1 | 4 | 4 | 5 | 4 | 3 | 5 | 5 | 5 | 6 | 5 | 5 | 5 | 5 | 6 | 5 |

2,4 D = 2,4-dichlorophenoxy acetic acid

TABLE III

BOOSTING OF HERBICIDE ACTIVITY IN THE LABORATORY

TIME LAPSED BETWEEN TREATMENT AND DETERMINATION OF RESULTS

| | DOSE | | 168 Hours (7 days) | | | 480 Hours (20 days) | | |
|---|---|---|---|---|---|---|---|---|
| PRODUCT | ppm | Kg a.p./ha | Ipo-moea | Ga-lium | Sor-ghum | Ipo-moea | Ga-lium | Sor-ghum |
| FUSICOCCYN | 50 | 0.1 | 3 | 2 | 1 | 3 | 2 | 1 |
| ATRAZINE | 50 | 0.1 | 1 | 1 | 0 | 6 | 1 | 0 |
| MIXTUE OF ATRAZINE AND FUSICOCCYN | 50 + 50 | 0.1 + 0.1 | 7 | 5 | 4 | 8 | 6 | 4 |

Atrazine = 2 chloro-6-ethylamino-4-isopropylamino-1,3,5-triazine

TABLE IV

BOOSTING OF HERBICIDE ACTIVITY IN THE LABORATORY

TIME LAPSED BETWEEN TREATMENT AND THE DETERMINATION

| | DOSE | | 120 Hours (5 days) | | | | 168 Hours (7 days) | | | | 480 Hours (20 d.) | | | |
|---|---|---|---|---|---|---|---|---|---|---|---|---|---|---|
| PRODUCTS | ppm | Kg a.p./ha | Echin-ochloa | Ipo-moea | Ga-lium | Sor-ghum | Echin-ochloa | Ipo-moea | Ga-lium | Sor-ghum | Echin-ochloa | Ipo-meoa | Ga-lium | Sor-ghum |
| FUSICOCCYN | 50 | 0.1 | 1 | 5 | 1 | 1 | 1 | 5 | 2 | 1 | 1 | 5 | 2 | 1 |
| LINURON | 50 | 0.1 | 0 | 0 | 0 | 1 | 0 | 1 | 0 | 2 | 3 | 1 | 2 | 5 |
| MIXTURE OF LINURON AND FUSICOCCYN | 50 + 50 | 0.1 + 0.1 | 2 | 6 | 6 | 3 | 7 | 6 | 6 | 7 | 7 | 6 | 6 | 7 |

Linuron = 3-(3,4-dichlorophenyl)-1-methoxy-1-methylurea

TABLE V

BOOSTING OF HERBICIDE ACTIVITY IN THE LABORATORY

LAPSED TIME BETWEEN TREATMENT AND DETERMINATION OF RESULTS

| | DOSE | | 480 Hours (20 days) | | | |
|---|---|---|---|---|---|---|
| PRODUCT | ppm | Kg of a.p./ha | Ipo-moea | Stel-laria | Vig-na | Sor-ghum |
| FUSICOCCYN | 10 | 0.02 | 1 | 5 | 7 | 2 |
| PHENMEDIPHAM | 150 | 0.3 | 3 | 6 | 6 | 0 |

TABLE V-continued

| | | | 480 Hours (20 days) | | | |
|---|---|---|---|---|---|---|
| PRODUCT | DOSE ppm | Kg of a.p./ha | Ipo-moea | Stel-laria | Vig-na | Sor-ghum |
| MIXTURE OF PHENMEDIPHAM AND FUSICOCCYN | 150 + 150 | 0.3 + 0.2 | 8 | 9 | 9 | 7 |

BOOSTING OF HERBICIDE ACTIVITY IN THE LABORATORY — LAPSED TIME BETWEEN TREATMENT AND DETERMINATION OF RESULTS

Phenmedipham = methyl-3-m.tolylcarbamoyloxy-phenylcarbamate.

EXAMPLE 2

BOOSTING OF THE HERBICIDE ACTIVITY BY FUSICOCCYN UNDER NATURAL ENVIRONMENTAL CONDITIONS (Field tests)

2 m² lots of surface infested naturally by the following plants: *AVENA FATUA*, LOLIUM Spp, FESTUCA Spp, ALOPECURUS, MYOSUROIDES, SINAPIS Spp, STELLARIA Spp, *POLYGONUM PERSICARIA, POLYGONUM AVICULARE*, ARTEMISIA Spp, *CONVOLVULUS ARVENSIS, ECHINOCHLOA CRUSGALLI*, SONCHUS Spp, SETARIA Spp, were sprinkled with fusicoccyn in the form of a hydroacetonic dispersion, or with Paraquat in an aqueous dispersion, or with a Paraquat+fusicoccyn mixture obtained by pouring the hydroacetonic fusicoccyn dispersion into the aqueous dispersion of the herbicide.

The quantity of sprinkled liquid amounted to 1000 lt/ha.

3, 4 and 6 days after the treatment, evaluations were made according to a value scale comprised between 0 and 9, wherein 0=no activity and 9=total activity (Tables VI-VII).

EXAMPLE 3

HARMLESSNESS OF THE FUSICOCCYN/SELECTIVE HERBICIDE MIXTURE ON USEFUL AGRICULTURAL CULTIVATIONS

Following the procedures described in Example 1, the following useful agrarian species: wheat, maize, beetroot, carrot, were sown in the pots, and kept in the conditioned room.

Thereafter, the small plants, respectively aged between 15 and 35 days, were sprinkled with fusicoccyn-herbicide mixtures obtained as described in Example 1. The quantity of liquid applied to the plants amounted to 2000 lt/ha.

After the treatment the small plants were maintained under observation in the same conditioned room, and the evaluations were carried out at intervals of time in hours indicated in Tables VIII to XI, infra, using the evaluation scale of Example 1.

As shown in the Tables, the selectivity of the herbicides under examination is not in the least influenced by the presence of the fusicoccyn.

TABLE VI

BOOSTING OF HERBICIDE ACTIVITY IN NATURAL CONDITIONS — DETERMINATION CARRIED OUT 4 DAYS AFTER THE TREATMENT

| PRODUCT | DOSE Kg of a.p./ha | A-vena | Lo-lium | Fes-tuca | Alope-curus myosy-roides | Sin-apis | Stel-laria | Poly-gonum persi-caria | Poly-gonum avicu-lare |
|---|---|---|---|---|---|---|---|---|---|
| FUSICOCCYN | 0.1 | 0 | 0 | 0 | 0 | 4 | 2 | 0 | 0 |
| PARAQUAT | 0.175 | 2 | 2 | 2 | 2 | 2 | 2 | 2 | 0 |
| MIXTURE OF PARAQUAT AND FUSICOCCYN | 0.175 + 0.1 | 5 | 7 | 7 | 7 | 7 | 8 | 4 | 2 |

TABLE VII

BOOSTING OF HERBICIDE ACTIVITY UNDER CONDITIONS OF A NATURAL ENVIRONMENT — LAPSED TIME BETWEEN TREATMENT AND DETERMINATION OF THE RESULTS

| | | 3 days | | | | | | | 6 days | | | | | | |
|---|---|---|---|---|---|---|---|---|---|---|---|---|---|---|---|
| PRODUCT | DOSE Kg of a.p./ha | Ar-tem-isia | Lo-lium | Con-vol-vo-lus | Poly-gonum | Echin-ochloa | Son-chus | Set-aria | Ar-tem-isia | Lo-lium | Con-vol-vo-lus | Poly-gonum | Echin-ochloa | Son-chus | Set-aria |
| FUSIOCOCCYN | 0.1 | 0 | 0 | 0 | 0 | 0 | 0 | 0 | 0 | 0 | 0 | 0 | 0 | 0 | 0 |
| PARAQUAT | 0.175 | 4 | 1 | 2 | 1 | 1 | 1 | 2 | 2 | 1 | 2 | 1 | 1 | 1 | 2 |
| PARAQUAT | 0.350 | 7 | 3 | 7 | 4 | 4 | 3 | 4 | 8 | 4 | 7 | 4 | 6 | 3 | 4 |
| MIXTURE OF PARAQUAT AND FUSICOCCYN | 0.175 + 0.025 | 4 | 3 | 4 | 3 | 5 | 3 | 3 | 4 | 3 | 4 | 3 | 6 | 3 | 4 |
| | 0.175 + 0.05 | 7 | 5 | 7 | 6 | 7 | 6 | 5 | 7 | 5 | 7 | 6 | 7 | 6 | 6 |
| | 0.175 + 0.1 | 8 | 6 | 7 | 6 | 7 | 6 | 6 | 8 | 6 | 7 | 6 | 8 | 6 | 6 | a.p. = active principle

TABLE VIII

SELECTIVITY DEVELOPED IN THE LABORATORY

| PRODUCT | DOSE ppm | DOSE Kg of a.p./ha | LAPSED TIME BETWEEN TREATMENT AND EVALUATIONS BEETROOT 480 Hours (20 days) |
|---|---|---|---|
| FUSICOCCYN | 10 | 0.02 | 0 |
| PHEN-MEDIPHAM | 150 | 0.3 | 0 |
| MIXTURE OF PHEN-MEDIPHAM AND FUSICOCCYN | 150 + 10 | 0.3 + 0.02 | 0 |

TABLE IX

SELECTIVITY DEVELOPED IN THE LABORATORY

| | DOSE | | WHEAT LAPSED TIME BETWEEN TREATMENT AND EVALUATIONS | | |
|---|---|---|---|---|---|
| PRODUCT | ppm | Kg of a.p./ha | 120 Hrs. (5 days) | 168 Hrs. (7 days) | 480 Hrs. (20 d) |
| FUSICOCCYN | 50 | 0.1 | 0 | 0 | 0 |
| 2,4 D | 125 | 0.25 | 0 | 0 | 0 |
| MIXTURE OF 2,4 D and FUSICOCCYN | 125 + 50 | 0.25 + 0.1 | 0 | 0 | 0 |

TABLE X

SELECTIVITY DEVELOPED IN THE LABORATORY

| | DOSE | | MAIZE LAPSED TIME BETWEEN TREATMENT AND EVALUATIONS | |
|---|---|---|---|---|
| PRODUCT | ppm | Kg of a.p./ha | 168 Hrs. (7 days) | 480 Hrs. (20 days) |
| FUSICOCCYN | 50 | 0.1 | 0 | 0 |
| ATRAZINE | 50 | 0.1 | 0 | 0 |
| MIXTURE OF ATRAZINE AND FUSICOCCYN | 50 + 50 | 0.1 + 0.1 | 0 | 0 |

TABLE XI

SELECTIVITY DEVELOPED IN THE LABORATORY

| | DOSE | | LAPSED TIME BETWEEN TREATMENT AND EVALUATIONS | | | | | |
|---|---|---|---|---|---|---|---|---|
| | | | WHEAT | | | CARROT | | |
| PRODUCT | ppm | Kg of a.p./ha | 120 hrs. (5 days) | 168 hrs. (7 days) | 480 hrs. (20 days) | 120 hrs. (5 days) | 168 hrs. (7 days) | 480 hrs. (20 days) |
| FUSICOCCYN | 50 | 0.1 | 0 | 0 | 0 | 0 | 0 | 0 |
| LINURON | 50 | 0.1 | 0 | 0 | 0 | 0 | 0 | 0 |
| FUSICOCCYN + LINURON | 50 + 50 | 0.1 + 0.1 | 0 | 0 | 0 | 0 | 0 | 0 |

We claim:

1. The method of boosting the activity of at least one herbicide selected from the group consisting of 1,1'-dimethyl-4,4'-dipyridilium chloride, 2-chloro-6-ethylamino-4-isopropylamino-1,3,5-triazine, and 3-(3,4-dichlorophenyl)-1-methoxy-1-methylurea, which consists in mixing the glucoside, fusicoccyn, with the herbicide in an amount of from one-fifteenth of the herbicide weight up to an amount equal to the herbicide weight.

2. The method of claim 1, in which the herbicide is 1,1'-dimethyl-4,4'-dipyridilium chloride.

3. The method of claim 1, in which the herbicide is 2-chloro-6-ethylamino-4-isopropylamino-1,3,5-triazine.

4. The method of claim 1, in which the herbicide is 3-(3,4-dichlorophenyl)-1-methoxy-1-methylurea.

5. A herbicidal composition the essential constituents of which are at least one herbicide selected from the group consisting of 1,1'-dimethyl-4,4'-dipyridilium chloride, 2-chloro-6-ethylamino-4-isopropylamino-1,3,5-triazine, and 3-(3,4-dichlorophenyl)-1-methoxy-1-methylurea, and the glucoside, fusicoccyn, in an amount of from one-fifteenth of the herbicide weight up to an amount equal to the herbicide weight.

6. A herbicidal composition according to claim 5, in which the herbicide is 1,1'-dimethyl-4,4'-dipyridilium chloride.

7. A herbicidal composition according to claim 5, in which the herbicide is 2-chloro-6-ethylamino-4-isopropylamino-1,3,5-triazine.

8. A herbicidal composition according to claim 5, in which the herbicide is 3-(3,4-dichlorophenyl)-1-methoxy-1-methylurea.

* * * * *